(12) United States Patent
Schloerholz

(10) Patent No.: US 10,391,783 B2
(45) Date of Patent: Aug. 27, 2019

(54) METHOD FOR OPERATING AN INKJET PRINTING MACHINE

(71) Applicant: HEIDELBERGER DRUCKMASCHINEN AG, Heidelberg (DE)

(72) Inventor: Matthias Schloerholz, Plankstadt (DE)

(73) Assignee: Heidelberger Druckmaschinen AG, Heidelberg (DE)

( * ) Notice: Subject to any disclaimer, the term of this patent is extended or adjusted under 35 U.S.C. 154(b) by 0 days.

(21) Appl. No.: 15/933,962

(22) Filed: Mar. 23, 2018

(65) Prior Publication Data

US 2018/0272744 A1    Sep. 27, 2018

(30) Foreign Application Priority Data

Mar. 27, 2017   (DE) ................. 10 2017 205 098

(51) Int. Cl.

| B41J 2/195 | (2006.01) |
| B41M 5/00 | (2006.01) |
| B41J 2/17 | (2006.01) |
| G01N 21/41 | (2006.01) |
| G01N 33/32 | (2006.01) |
| B41J 3/407 | (2006.01) |
| B41J 29/46 | (2006.01) |

(52) U.S. Cl.
CPC ............ *B41J 2/195* (2013.01); *B41J 2/1707* (2013.01); *B41J 3/4073* (2013.01); *B41J 29/46* (2013.01); *B41M 5/0023* (2013.01); *B41M 5/0088* (2013.01); *G01N 21/41* (2013.01); *G01N 33/32* (2013.01)

(58) Field of Classification Search
CPC ................................... B41J 2/195; B41J 2/20
See application file for complete search history.

(56) References Cited

U.S. PATENT DOCUMENTS

| 4,834,533 | A | 5/1989 | Horike et al. |
| 7,221,440 | B2 | 5/2007 | McCann et al. |
| 7,522,281 | B2 | 4/2009 | Fischer |
| 2003/0020790 | A1* | 1/2003 | Kotaki ................ B41J 2/17513 347/86 |
| 2006/0044550 | A1* | 3/2006 | McCann ................ G01N 21/43 356/128 |

(Continued)

FOREIGN PATENT DOCUMENTS

| CN | 101357540 A | 2/2009 |
| JP | S62206431 A | 9/1987 |

(Continued)

OTHER PUBLICATIONS

Rathjen et al., "Electrical Measurement of Ink Sedimentation", 30th International Conference on Digital Printing Technologies (NIP 30): digital fabrication and digital printing, Sep. 7-11, 2014, pp. 342-346, ISBN 978-1-5108-1438-7.

*Primary Examiner* — Shelby L Fidler
(74) *Attorney, Agent, or Firm* — Laurence A. Greenberg; Werner H. Stemer; Ralph E. Locher

(57) ABSTRACT

In a method for operating an inkjet printing machine, a condition of an ink is determined. A sedimentation and/or agglomeration of a pigmented ink is determined by refractometry, i.e. the value of the refractive index of the ink is measured with a refractometer and compared with a stored value with computer assistance.

9 Claims, 3 Drawing Sheets

(56) References Cited

U.S. PATENT DOCUMENTS

| | | | |
|---|---|---|---|
| 2008/0204749 A1* | 8/2008 | Haddock | G01N 15/0205 356/335 |
| 2011/0242158 A1* | 10/2011 | Takata | B41J 2/175 347/7 |
| 2013/0063516 A1* | 3/2013 | Sakai | B41J 29/38 347/19 |
| 2013/0147870 A1* | 6/2013 | Yeh | B41J 2/2052 347/15 |
| 2016/0216191 A1 | 7/2016 | Balashanmugam et al. | |
| 2018/0072062 A1* | 3/2018 | Shindo | B41J 2/16508 |

FOREIGN PATENT DOCUMENTS

| | | |
|---|---|---|
| JP | 2004239631 A | 8/2004 |
| JP | 2011050823 A | 3/2011 |
| JP | 2011056370 A | 3/2011 |
| JP | 2012024997 A | 2/2012 |
| WO | 2016118228 A1 | 7/2016 |

\* cited by examiner

METHOD FOR OPERATING AN INKJET PRINTING MACHINE

CROSS-REFERENCE TO RELATED APPLICATION

This application claims the priority, under 35 U.S.C. § 119, of German application DE 10 2017 205 098.5, filed Mar. 27, 2017; the prior application is herewith incorporated by reference in its entirety.

BACKGROUND OF THE INVENTION

Field of the Invention

The present invention relates to a method having the features of the preamble of the main independent claim.

The invention lies in the technical field of the graphic industry and, there, in particular in the region of industrial inkjet printing on three-dimensional objects or on flat substrates, i.e. the application of liquid ink to free-form surfaces, preferably of plastic or metal, or to sheet or web printing materials, preferably of paper, board or plastic.

The application of liquid ink is carried out in the known drop-on-demand (DOD) inkjet printing method by a printed image being generated on the surface, wherein an inkjet print head (head for short) with individually drivable nozzle openings generates extremely fine ink droplets, preferably in the picoliter range, corresponding to the image to be printed, and transfers these without contact onto the surface as printed dots.

During the printing of pigmented inks, there can be the problem that the inks sediment, i.e. that the pigment particles begin to be deposited and to form a sediment in the ink supply device, in particular when little ink is printed or used and the ink therefore moves little for too long a time or even remains unmoved. During the printing of three-dimensional objects, this problem can occur when the print head is guided along the contour of the surface, printing only slowly and consequently using little ink, or is moved without printing for re-positioning. The printed image can exhibit deficiencies as a result of the sedimentation. In this way, the printing costs can rise. Pigmented inks in storage containers or sales packages likewise tend to sedimentation. In addition, the manufacturers usually provide the inks with an expiry date. In the event of low ink consumption, there can therefore also be the problem that large quantities of ink are disposed of and the printing costs rise. This is also correspondingly true of the agglomeration of pigments in liquid inks.

U.S. Pat. No. 7,221,440 B2 discloses the monitoring by measurement of the concentration of an ink by using a refractometer. The problem of sedimentation or agglomeration is neither addressed nor solved. Instead, an increase in concentration as a result of evaporation during printing breaks is described as a problem. It is also disclosed that the measurement is suitable only for low-absorbent inks, which is to say rather not for white ink.

U.S. Pat. No. 4,834,533 discloses the measurement of the refractive index of an ink, without specifying the purpose. It is also disclosed that dyes are deposited on a fiber of a refractometer and, as a result, can disrupt measurement. The device disclosed therefore appears to be less suitable to eliminate the problem of sedimentation or agglomeration.

SUMMARY OF THE INVENTION

Against this background, it is an object of the present invention to devise a method which is improved as compared with the prior art and which makes it possible to avoid increasing the printing costs on account of ink sedimentation and/or agglomeration.

According to the invention, this object is achieved by a method as claimed in the independent claim. Advantageous and therefore preferred developments of the invention can be gathered from the sub-claims and from the description and the drawings.

A method according to the invention for operating an inkjet printing machine, a condition of an ink being determined, is distinguished by the fact that the sedimentation and/or agglomeration of a pigmented ink is determined by refractometry, i.e. the value of the refractive index n of the ink is measured with a refractometer and, with computer assistance, is compared with a stored value.

The invention advantageously makes it possible to avoid an undesired increase in the printing costs on account of ink sedimentation, in that possible sedimentation of a pigmented ink is determined by refractometry and is thus preferably detected in good time for countermeasures. The use of a refractometer additionally makes it possible to determine the level of sedimentation quickly, precisely, reliably and economically. This is correspondingly also true of the agglomeration of pigments in liquid inks.

Investigations were carried out within the context of comprehensive development work on inkjet printing machines for printing objects and, contrary to initial assumptions, it was verified that the level of ink sedimentation and/or agglomeration can be determined with sufficient accuracy by refractometry—for the relevant printing applications and inks used in the process.

As a result of the undesired (but, according to the invention, determinable and therefore also avoidable) irreversible sedimentation and/or agglomeration, it is possible for so-called depletion of the liquid ink to occur. The refractive index of the ink rises in the process, i.e. a refractive index determined by refractometry that rises over time points to sedimentation and/or agglomeration of pigments and can be used as a trigger for countermeasures, such as, for example, stirring or recirculating (or even replacing) the ink, in particular in order to prevent irreversible depletion. In the most beneficial case, by means of the measures initiated, the ink can be returned or virtually returned to the condition when delivered by the manufacturer. In the inks investigated, a rise in the refractive index was actually observed, but it is alternately also possible that the refractive index will fall as a result of the sedimentation and/or agglomeration.

An example of a set of measured values of the refractive index n from refractometric measurements according to the invention on a commercially available white ink:
Measurement from original container (after slight shaking): n=1.43 to 1.445;
Measurement of an ink at rest after mixing: n=1.425 to 1.44;
Measurement of an ink at rest: n=1.48 to 1.485; and
Measurement of an ink at rest before mixing: n=1.475 to 1.48.

It can be seen that the refractive index n of the ink rises when the ink is at rest, and that, conversely, the refractive index n of the ink falls when the ink is mixed or stirred. The value of the refractive index n of about 1.47 can be used as a limiting value, in particular in the present example, below which the ink can be printed and above which mixing or stirring, etc., is required before printing. If, as a result of the mixing or stirring, etc. of the ink, the index does not fall below a value of about 1.47, further measures can be taken, for example intensive stirring (longer and/or faster stirring), ultrasonic stirring (i.e. the mixing of the ink by using an ultrasound source) or even the replacement of the ink.

The fluctuations in the measurements can be explained, inter alia, by the measurement structure in the test environment: for the purpose of measurement, an ink drop was put onto a horizontally arranged glass plate (measuring location) in the handheld measuring instrument. In the time (a few seconds) between application and measurement, the ink may already sediment, which can be measured in the lowest ink layer, which is to say in the gas/ink interface. When the invention is used in the industrial product environment, the measurement would therefore preferably be carried out on an upright glass plate of the measuring instrument or a measuring probe integrated into the ink supply device. Provision can also be made to allow a defined time to elapse following the application of the ink to the glass plate, and only then to measure. As a result, the measurements would be comparable with one another.

The effect of the (actually undesired) sedimentation on the measuring instrument or its glass plate can, however, also be used specifically for measurement: following the application of a defined quantity of ink, the sedimentation on the glass plate begins and the measured refractive index falls until a quasi-closed pigment layer has been deposited on the glass as a boundary layer. The refractive index then no longer changes or no longer changes substantially. The time interval until this constant refractive index value is reached and the difference in the refractive index within this time interval would once more depend on the initial concentration of the pigment in the ink, so that in this way the (initial) pigment concentration of the ink can be determined.

The refractometric determination is preferably carried out by a refractometer which is provided or arranged in the machine, in particular in its ink supply device. Alternatively, the determination can also be carried out with a mobile refractometer, for example with an appropriately equipped handheld instrument, by the machine operator or by service employees.

A preferred development of the invention can be distinguished by the fact that the measurement is carried out directly after stirring or recirculation (pumping) of the ink. As a result of the stirring, etc., the sediment and/or agglomerates formed are wholly or partly resolved. However, in dead spaces of an ink supply device, it is still possible for sediment residues and/or agglomerate residues to be present, which means that it is possible for not all the pigments to be brought into the liquid phase of the ink again as a result of the stirring, and for the liquid ink to be "depleted". However, by means of the refractometric measuring method, it is possible to determine whether the liquid ink once more has sufficiently non-sedimented and non-agglomerated pigments, in order to be able to continue printing in the required quality.

A preferred development of the invention can be distinguished by the fact that the sedimentation and/or agglomeration is/are measured in the liquid phase of the ink.

A preferred development of the invention can be distinguished by the fact that the sedimentation and/or agglomeration is/are measured in an ink tank or in a storage container or an ink line.

A preferred development of the invention can be distinguished by the fact that the sedimentation and/or agglomeration is/are measured continuously or quasi-continuously, i.e. preferably at predefined time intervals or cyclically, for example approximately once per second or per 10 seconds or per minute. In this way, a change in the condition of the ink over time can be detected and, for example, the rate of sedimentation and/or the rate of agglomeration of an ink (during printing and/or printing breaks) can be determined. In addition, sedimentation-induced and/or agglomeration-induced aging of the ink can be determined and, from this, a necessary ink change caused by sedimentation and/or agglomeration can be forecast.

A preferred development of the invention can be distinguished by the fact that, depending on the value of a deviation obtained from the comparison, in particular a difference, one of the following (counter-) measures is taken:

a) printing with the ink without stirring,
b) printing with the ink with simultaneous stirring,
c) printing with the ink after stirring,
d) intensifying the stirring, in particular longer and/or faster stirring,
e) outputting a warning against excessively high sedimentation,
f) emptying an ink tank and/or an ink storage container,
g) flushing an ink tank and/or an ink storage container and/or an ink line and/or an inkjet print head with a cleaning liquid, and
h) changing the ink, that is to say filling with an ink other than that emptied.

A preferred development of the invention can be distinguished by the fact that the sedimentation-dependent and/or agglomeration-dependent refractive index of a white ink is determined, in particular in an inkjet printing machine for printing three-dimensional objects. White ink and the relatively large and thus heavy white pigments of the ink or a liquid primer tend to particularly fast and therefore intense sedimentation.

A preferred development of the invention can be distinguished by the fact that, in order to determine the type of ink, the measured, sedimentation-dependent and/or agglomeration-dependent refractive index is compared with at least one stored type-specific refractive index.

A preferred development of the invention can be distinguished by the fact that, in order to determine the color of the ink, the measured, sedimentation-dependent and/or agglomeration-dependent refractive index is compared with at least one stored color-specific refractive index.

Investigations were also carried out and it was verified that a specific ink, e.g. of a specific type, of a specific color (CMYK or white) or from a specific manufacturer, can be detected by refractometry. The method can therefore also be carried out in an advantageous way in order to determine whether the correct ink or a wrong ink is in use. Printing with wrong inks, in particular inks not approved for the machine, or transposed inks, for example following an ink change, can therefore be prevented and corresponding costs avoided.

A preferred development of the invention can be distinguished by the fact that, in order to determine the age of the ink, the measured, sedimentation-dependent and/or agglomeration-dependent refractive index is compared with at least one stored age-specific or aging-specific refractive index. Investigations were also carried out and it was verified that the age or the pigment-based state of aging of a specific ink, for example of a specific type, a specific color (CMYK or white) or from a specific manufacturer can be detected by refractometry. The method can therefore also advantageously be carried out in order to determine whether an ink can be disposed of or can still be printed.

Other features which are considered as characteristic for the invention are set forth in the appended claims.

Although the invention is illustrated and described herein as embodied in a method for operating an inkjet printing machine, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
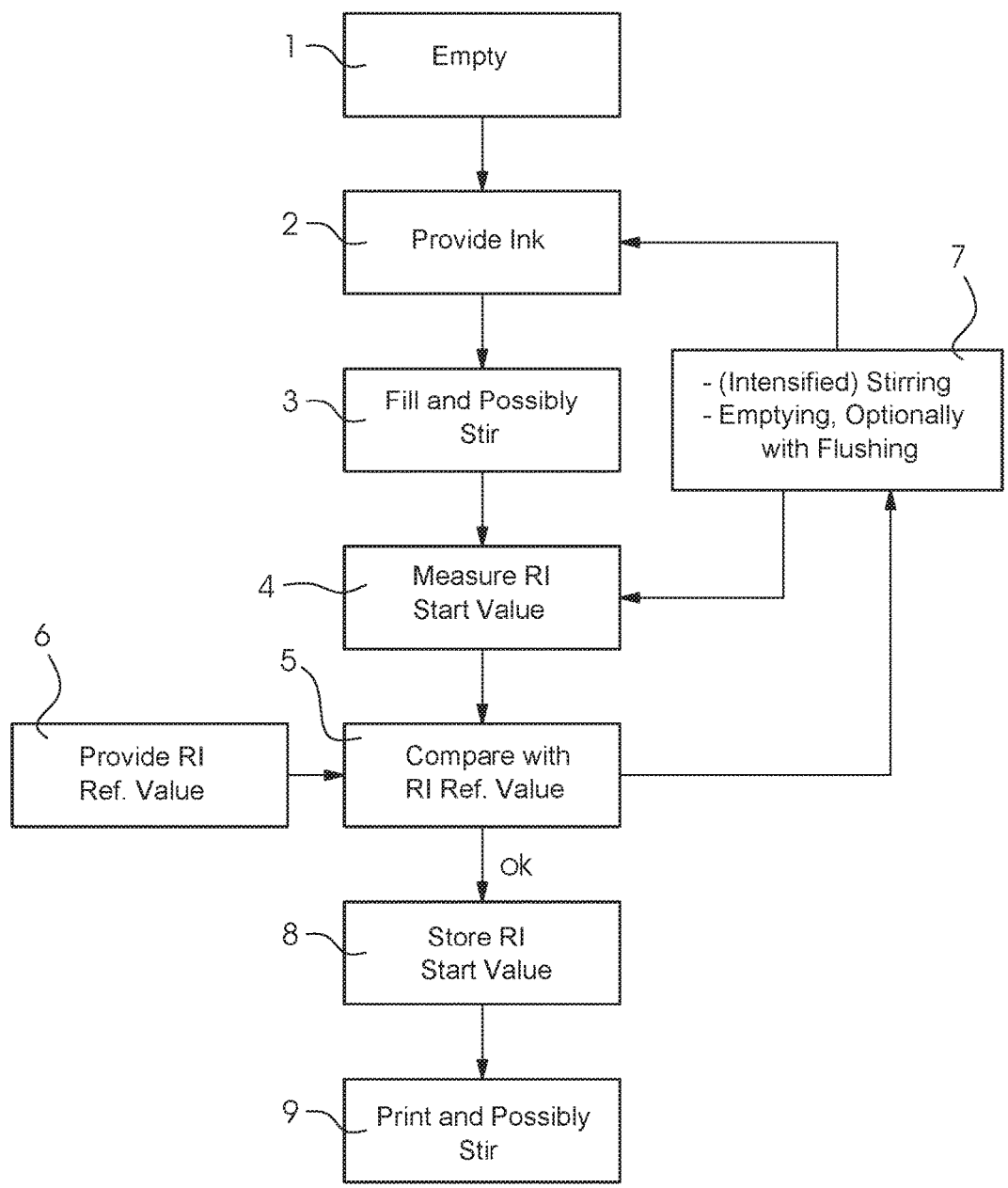
FIG. 1 is a flow chart showing a preferred exemplary embodiment of a method according to the invention.

Referring now to the figures of the drawings in detail and first, particularly to FIG. 1 thereof, there is shown a flow-chart of a series of method steps of a preferred exemplary embodiment of a method according to the invention. The method steps will be explained below (with regard to the designations, reference is also made to FIG. 3).

Step 1 (optional): An ink supply device 17 of an inkjet printing machine 18 or its ink tank 20 and/or ink storage container and possibly its ink lines 22a, 22b, 25 and 31a is/are emptied of liquid ink 21, 24.

Step 2: Liquid ink 24 is provided, i.e. the ink is put into storage container 23 (or an already filled storage container is provided).

Step 3: The ink 24 from the storage container 23 is brought or put into the ink tank 20, preferably pumped, and is present there as ink 21. Optionally, the ink 21 is stirred by using a stirrer 27. The ink is brought, preferably pumped, via an ink line 22a to at least one inkjet print head 22 and back to the ink tank 20 via an ink line 22b.

Step 4: A starting value $n_{Start}$ of a refractive index n of the ink is measured. The measurement can be carried out at one of the following points: preferably with a refractometer 30 in the storage container 23 or with the refractometer 31 in an ink line 31a, 31b ("bypass") on the storage container 23; or with the refractometer 32 in the ink line 22a, 22b; or with the refractometer 33 in the ink tank 20. The measured value n can be stored.

Step 5: The measured starting value $n_{Start}$ of the refractive index n is compared by computer with a—preferably likewise stored (see step 6)—reference value of the refractive index $n_{Ref}$. Preferably, a difference is formed.

Step 6: The—preferably stored—reference value of the refractive index $n_{Ref}$ is provided for the comparison by computer. The reference value can, for example, originate from the ink manufacturer or can be determined from previous measurements (e.g. by means of averaging).

Step 7: Depending on or in the event of an excessively high value of a deviation Δn of n relative to $n_{Ref}$ that is obtained from the comparison, one of the following measures is taken: intensified stirring (longer and/or faster; with stirrer 27 and/or 28), after that step 4: emptying (the ink tank 20 and/or the ink storage container 23), optionally combined with flushing with a cleaning liquid, after that step 2.

Step 8: Depending on or in the event of a value that is not excessively high (or is suitable) of a deviation Δn of n relative to $n_{Ref}$ that is obtained from the comparison, the measured starting value $n_{Start}$ of the refractive index n is stored, i.e. preferably stored by computer.

Step 9: The printing of a print job is started, i.e. the inkjet print head 22 transfers the image to be printed in the form of ink drops to the surface 19 (of a three-dimensional object or a flat substrate). Optionally, the ink 21 is stirred by using a stirrer 27.

Figure 2:
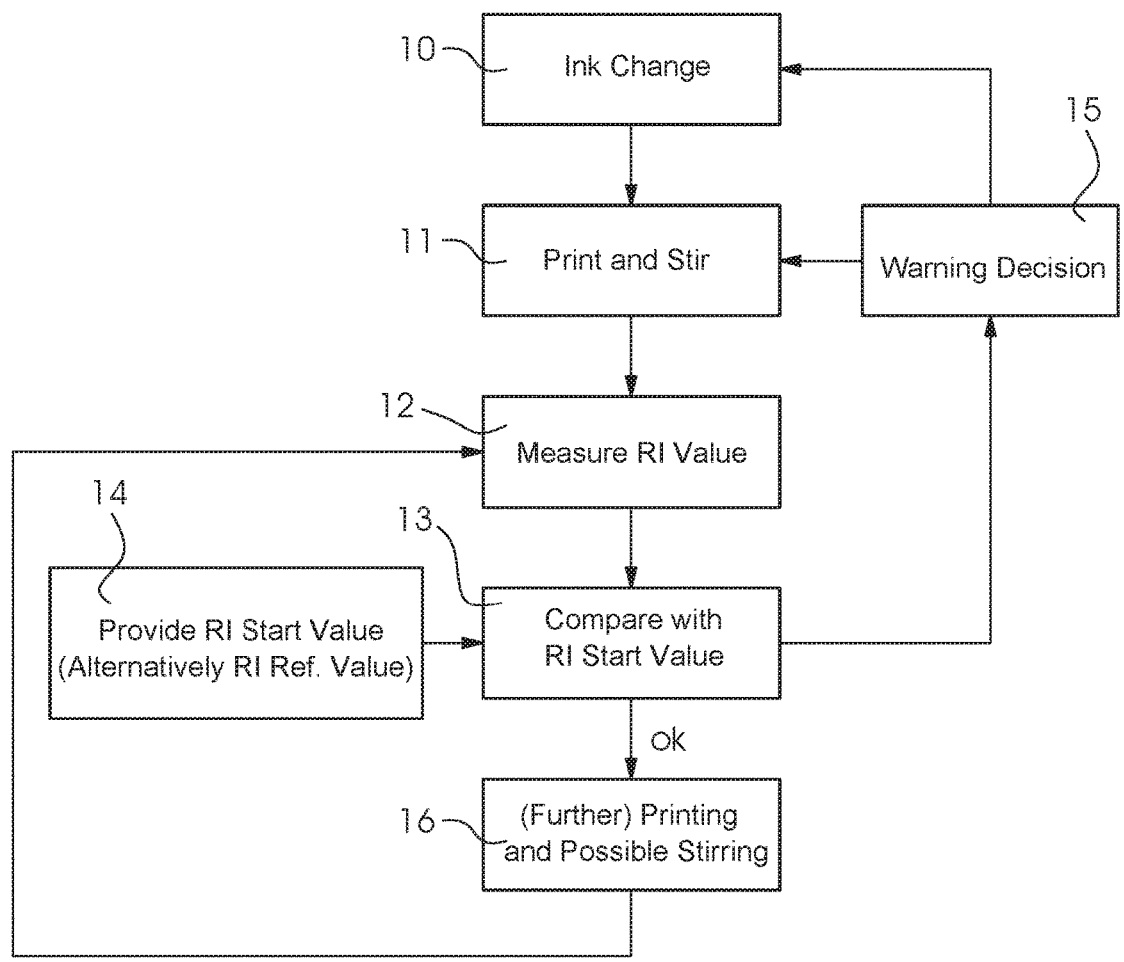
FIG. 2 is a flow chart showing a preferred exemplary embodiment of a method according to the invention.

FIG. 2 shows a flowchart of a series of further method steps of a preferred exemplary embodiment of a method according to the invention.

Step 10 (optional): After a print job has been completed, an ink change is made. The steps to be carried out for this purpose can coincide with steps 1 to 3 (see FIG. 1).

Step 11: The inkjet print head 22 prints and a print job is carried out. During the printing, the ink 21 and/or 24 can optionally be stirred or recirculated.

Step 12: During the printing, a determination or measurement of the value of the refractive index $n_{current}$ of the ink is carried out (continuously or quasi-continuously).

Step 13: The measured value of the refractive index $n_{current}$ is compared by computer with a—preferably stored (see steps 6, 8 and 14)—starting value $n_{Start}$ or reference value of the refractive index $n_{Ref}$. The difference is preferably formed.

Step 14: The—preferably stored—starting value of the refractive index $n_{Start}$ (or alternatively the reference value of the refractive index $n_{Ref}$) is provided for the comparison by computer.

Step 15: Depending on or in the event of an excessively high value of a deviation Δn of $n_{current}$ relative to $n_{Start}$ (or alternatively $n_{Ref}$) that is obtained from the comparison, one of the following measures is taken: outputting a warning against excessively high sedimentation (possibly with the recommendation to change the ink); computer-aided gathering of a decision for or against an ink change. Depending on the reaction of the operator, an ink change can be carried out (further with step 10), or printing can be continued (further with step 11). The decision can also be made by computer, for example by predefining a limiting value for the deviation Δn. Alternatively, the following can also be initiated: intensified stirring (longer and/or faster; with stirrer 27 and/or 28), after that or simultaneously, step 11.

Step 16: Depending on or in the event of a value that is not excessively high (or is suitable) of a deviation Δn of $n_{current}$ relative to $n_{Start}$ (or alternatively $n_{Ref}$) that is obtained from the comparison, printing is continued and, possibly, stirring is continued. Then, a measurement according to step 12 can be carried out again.

Figure 3:
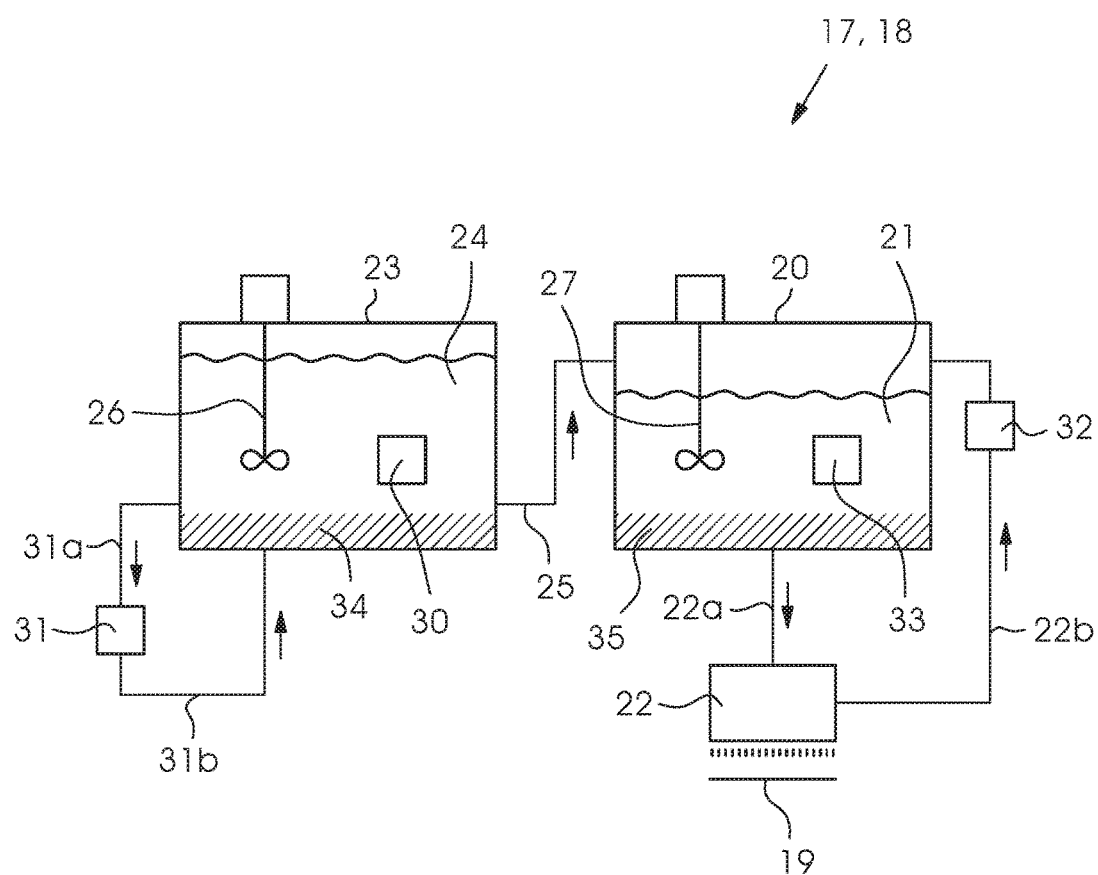
FIG. 3 is an illustration showing a device during the performance of a preferred exemplary embodiment of a method according to the invention.

FIG. 3 shows a device during the performance of a preferred exemplary embodiment of a method according to the invention. Liquid ink 21 is accommodated in an ink tank 20. The ink is led to an inkjet print head 22 and non-printed ink is led back to the tank (via ink lines 22a, 22b). Ink 24 is likewise accommodated in a storage container 23. The storage container can preferably accommodate more ink than the tank; it can be formed, for example, as a can or a barrel. The ink is led to the tank 20 (via a line 25). A stirrer 26 is provided in the container 23, a stirrer 27 in the tank 20. Alternatively, it is also possible for only one of the two stirrers to be provided. The stirrers are intended to prevent or re-mix sediments 34, 35.

FIG. 2 additionally shows the locations at which measuring devices or sensors can be arranged: a refractometer 30 in the container 23, a refractometer 31 in a line 31a, 31b, a refractometer 32 in the line 22b (or alternatively in the line 22a) and/or a refractometer 33 in the tank 20.

The following is a summary list of reference numerals and the corresponding structure used in the above description of the invention:

1 to 16 Method steps
17 Ink supply device
18 Inkjet printing machine
19 Surface
20 Ink tank
21 Ink
22 Inkjet print head
22a, 22b Ink lines
23 Ink storage container
24 Ink
25 Ink line
26, 27 Stirrer
30, 31 Refractometer
31a, 31b Ink line
32, 33 Refractometer
34, 35 Sediments

The invention claimed is:

1. A method for operating an inkjet printing machine, which comprises the steps of:
providing a refractometer;
determining a condition of a pigmented ink by performing the further steps of:
measuring a value of a refractive index of the pigmented ink with the refractometer;
determining a sedimentation and/or agglomeration of the pigmented ink based on a deviation of the value of the refractive index from a reference value of the refractive index of the pigmented ink by comparing the value of the refractive index with a stored reference value with a computer;
initiating a corrective measure in the printing machine for reducing the refractive index when the deviation exceeds a selected deviation;
comparing a measured, sedimentation-dependent and/or agglomeration-dependent refractive index with at least one stored type-specific refractive index for determining a type of ink;
starting a print job by applying ink with a print head of the printing machine when the deviation is below an acceptable level.

2. The method according to claim 1, which further comprises carrying out a measurement directly after stirring the pigmented ink.

3. The method according to claim 1, which further comprises measuring the sedimentation and/or agglomeration in a liquid phase of the pigmented ink.

4. The method according to claim 1, which further comprises measuring the sedimentation and/or agglomeration in an ink tank or an ink storage container or an ink line.

5. The method according to claim 1, which further comprises measuring the sedimentation and/or agglomeration continuously or quasi-continuously.

6. The method according to claim 1, wherein depending on a value of a deviation obtained from a comparison, one of the following steps is taken:
printing with the pigmented ink without stirring;
printing with the pigmented ink with simultaneous stirring;
printing with the pigmented ink after the stirring;
intensifying the stirring, namely longer and/or faster stirring;
outputting a warning upon detection of a high sedimentation;
computer-aided gathering of a decision for or against an ink change;
emptying an ink tank and/or an ink storage container;
flushing the ink tank and/or the ink storage container and/or an ink line and/or an inkjet print head with a cleaning liquid; and
changing out the pigmented ink.

7. The method according to claim 1, which further comprises determining a sedimentation-dependent and/or agglomeration-dependent refractive index of a white ink in the inkjet printing machine for printing three-dimensional objects.

8. A method for operating an inkjet printing machine, which comprises the steps of:
providing a refractometer;
determining a condition of a pigmented ink by performing the further steps of:
measuring a value of a refractive index of the pigmented ink with the refractometer;
determining a sedimentation and/or agglomeration of the pigmented ink based on a deviation of the value of the refractive index from a reference value of the refractive index of the pigmented ink by comparing the value of the refractive index with a stored reference value with a computer;
initiating a corrective measure in the printing machine for reducing the refractive index when the deviation exceeds a selected deviation;
comparing a measured, sedimentation-dependent and/or agglomeration-dependent refractive index with at least one stored color-specific refractive index for determining a color of the pigmented ink;
starting a print job by applying ink with a print head of the printing machine when the deviation is below an acceptable level.

9. A method for operating an inkjet printing machine, which comprises the steps of:
providing a refractometer;
determining a condition of a pigmented ink by performing the further steps of:
measuring a value of a refractive index of the pigmented ink with the refractometer;
determining a sedimentation and/or agglomeration of the pigmented ink based on a deviation of the value of the refractive index from a reference value of the refractive index of the pigmented ink by comparing the value of the refractive index with a stored reference value with a computer;
initiating a corrective measure in the printing machine for reducing the refractive index when the deviation exceeds a selected deviation;
comparing measured, sedimentation-dependent and/or agglomeration-dependent refractive index with at least one stored age-specific or aging-specific refractive index for determining an age of the pigmented ink;
starting a print job by applying ink with a print head of the printing machine when the deviation is below an acceptable level.

* * * * *